United States Patent [19]
Petit et al.

[11] Patent Number: 5,328,099
[45] Date of Patent: Jul. 12, 1994

[54] COMPRESSED GAS DEVICE FOR SPRAYING A SINGLE DOSE OF A FLUID SUBSTANCE IN FINELY DIVIDED FORM

[75] Inventors: Ludovic Petit, Amfreville la Campagne; Philippe Solignac; Pascal Bruna, both of Rouen, all of France

[73] Assignee: Etablissements Valois, Le Neubourg, France

[21] Appl. No.: 77,059

[22] Filed: Jun. 16, 1993

[30] Foreign Application Priority Data

Jun. 16, 1992 [FR] France .................. 92 07250

[51] Int. Cl.⁵ .............................................. B05B 7/24
[52] U.S. Cl. ................................. 239/372; 239/325; 239/302; 239/570; 222/631
[58] Field of Search ............ 239/325, 372, 590, 590.3, 239/590.5, 302, 570; 222/631, 632, 633; 137/268, 467

[56] References Cited

U.S. PATENT DOCUMENTS

| | | |
|---|---|---|
| 2,223,611 | 12/1940 | Gross . |
| 2,515,193 | 7/1950 | Chester .................. 222/633 |
| 2,718,987 | 9/1955 | Kimball .................. 222/633 |
| 2,731,299 | 1/1956 | Bramming .................. 239/590.5 |
| 3,127,110 | 3/1964 | Reynolds .................. 239/590.3 |
| 4,017,007 | 4/1977 | Riccio .................. 222/631 |
| 4,162,749 | 7/1979 | Bennett .................. 222/633 |
| 4,294,410 | 10/1981 | Gueret .................. 239/590.5 |

FOREIGN PATENT DOCUMENTS 2256084 12/1974 France .
518744 3/1972 Switzerland .
1012895 9/1991 World Int. Prop. O. .......... 222/631

Primary Examiner—Andres Kashnikow
Assistant Examiner—Christopher G. Trainor
Attorney, Agent, or Firm—Sughrue Mion, Zinn, Macpeak and Seas

[57] ABSTRACT

A compressed gas device is disclosed for spraying a single dose of a fluid substance in finely divided form. The device comprises a tank containing the single dose having an inlet orifice for compressed gas, and an outlet orifice. The device further comprises a manually actuated gas pump having a gas supply communicating with the inlet orifice of the tank via an intermediate channel. The intermediate channel has a length of narrowed section that is closed in a sealed manner by a plug which is held in the narrowed section so that when the pressure of the gas supplied by the pump reaches a predetermined threshold, the plug is expelled towards the tank to open the intermediate channel. The device includes an abutment element to limit the displacement of the plug towards the outlet orifice of the tank of substance. The abutment element is constructed to guarantee that the compressed air can continue to floe through the outlet orifice when the plug is in its abutment position.

22 Claims, 5 Drawing Sheets

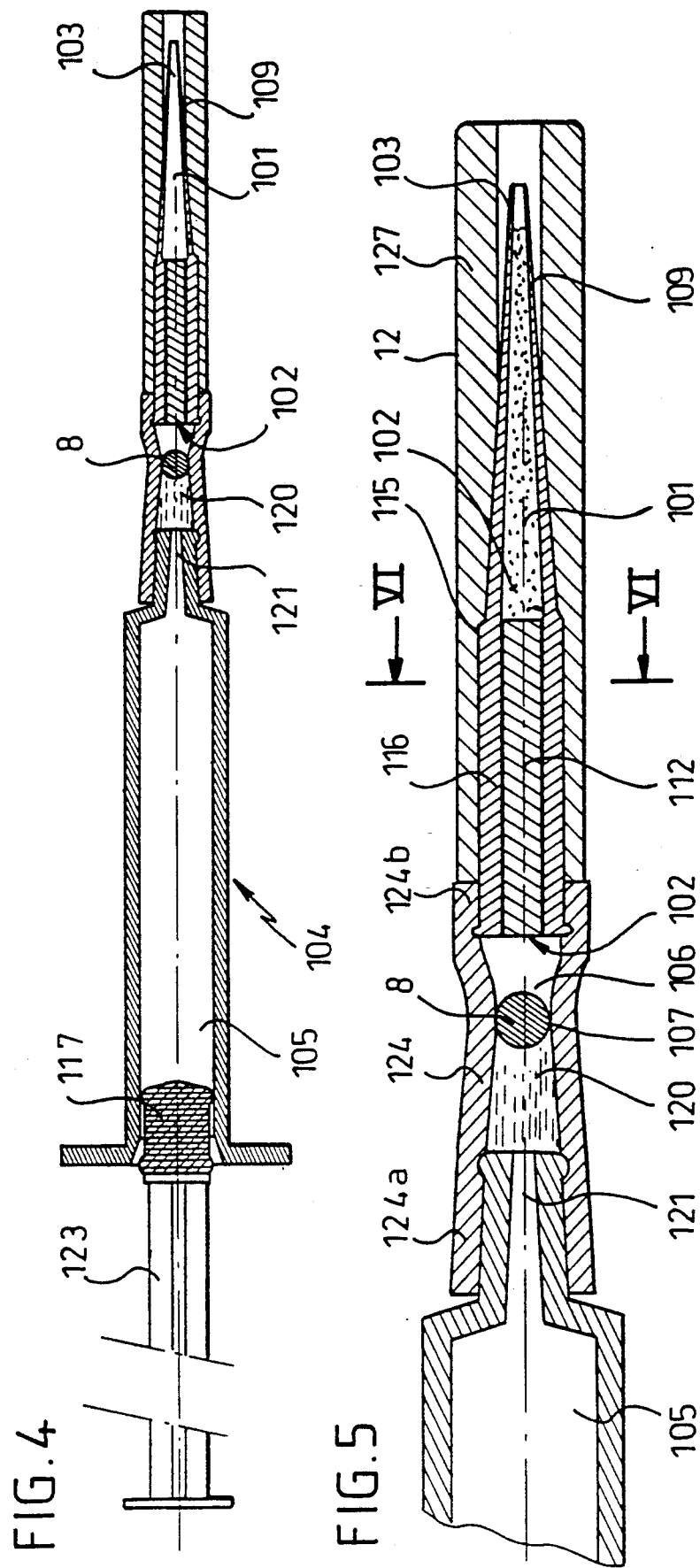

COMPRESSED GAS DEVICE FOR SPRAYING A SINGLE DOSE OF A FLUID SUBSTANCE IN FINELY DIVIDED FORM

The present invention relates to a compressed gas device for spraying a single dose of a fluid substance in finely divided form.

More particularly, the invention applies to such devices intended for spraying a single dose of a medicine in solid powder form or in liquid form. Such devices are generally used for nose sprays.

Document CH-A-518 744 discloses a compressed gas device for spraying a single dose of a fluid substance in finely divided form, the device comprising:

a tank containing said single dose, said tank having an inlet orifice for compressed gas and an outlet orifice;

manually-actuated gas compression means, said gas compression means comprising a supply of gas communicating with the inlet orifice of the tank via an intermediate channel including a length of narrowed section, said length of narrowed section being closed in sealed manner by a plug which is held in said length of narrowed section so that when the pressure of the gas contained in the supply of gas reaches a predetermined threshold, said plug is expelled from said length of narrowed section towards the tank of substance, thereby opening said intermediate channel;

the device further comprising means for limiting the displacement of the plug towards the outlet orifice of the tank of substance, thereby defining an abutment position for the plug.

In the above-mentioned document, the tank of substance includes a convergent portion which converges towards the outlet orifice and which constitutes the means for limiting displacement of the plug towards the outlet orifice of the tank. The plug is in the form of a spherical bead, and as a result there is a non-negligible risk of the bead obstructing the outlet orifice before all of the substance contained in the tank has been expelled.

An object of the present invention is to avoid that drawback.

The present invention therefore provides a compressed gas device as defined above and characterized in that said means for limiting displacement of the plug include means for guaranteeing that the compressed gas can continue to flow when the plug is in its abutment position.

In an embodiment of the invention, the tank of substance includes a convergent portion which converges towards the outlet orifice, said convergent portion constituting said means for limiting the movement of the plug, and said convergent portion including inside relief constituting said means for guaranteeing that the compressed gas can flow.

In another embodiment, the substance is a solid powder material, the tank of substance includes a fixed barrier which holds the dose of powder material in a position that is distant from the inlet orifice for compressed gas, said fixed barrier constituting said means for limiting the movement of the plug, and said means for guaranteeing that the compressed gas can flow include at least one opening through said fixed barrier. Advantageously, in this embodiment, the plug comes into contact with said fixed barrier, and said plug has sufficient kinetic energy for the shock of the plug against the fixed barrier to cause the dose of powder material to be unstuck from said fixed barrier. The said fixed barrier may be an element in the form of a diaphragm, advantageously having a certain degree of flexibility. The said fixed barrier may alternatively include a solid central rod having at least one axial lateral groove constituting said at least one through opening for the compressed gas flow.

In another embodiment, the plug includes an enlarged catch which co-operates with the length of narrowed section of the intermediate channel to limit the movement of the plug towards the tank of substance, said catch including at least one opening which constitutes said means for guaranteeing that the compressed gas can flow.

Advantageously, when said substance is a solid powder material, and at the moment when said means for limiting the movement of the plug stop displacement of said plug, said plug possesses sufficient kinetic energy to transmit a shock to said powder material that ensures that said powder material breaks up.

In an advantageous embodiment, said substance is a solid powder material, said tank of substance includes a convergent portion that converges towards the outlet orifice, said convergent portion being of a shape and the outlet orifice being of a section that are adapted to enable the powder material to be retained by a bridging effect in the vicinity of the outlet orifice while the device is being handled prior to being actuated. Advantageously, in this case, when said means for limiting the movement of the plug stop the displacement of the plug, said plug possesses sufficient kinetic energy to transmit a shock to said powder material that breaks the bridging of the powder material and thus facilities spraying of the powder material through the outlet orifice by the flow of compressed gas. To ensure a good bridging effect with usual pharmaceutical powders, the outlet orifice from the tank of substance may have a diameter that is less than or equal to 1.5 mm, possibly being less than or equal to 1 mm, possibly less than or equal to 0.5 mm.

In an embodiment:

the tank of said substance is included in a pusher-endpiece having a hollow cylindrical rear portion in communication with the compressed gas inlet orifice of the tank;

the gas compression means include a hollow piston which is engaged in the rear portion of the pusher-endpiece, and a cylinder provided with an end wall, the cylinder sliding axially over the piston; and the hollow piston defines the intermediate channel.

Advantageously, the hollow piston is made of a flexible thermoplastic material, such as polyethylene.

In another embodiment, the said intermediate channel includes a supply of liquid, and liquid-retaining means are disposed between the plug and the supply of gas. Advantageously, the liquid-retaining means are constituted by a capillary channel.

In another embodiment, the substance is a solid powder material, the tank of substance includes a fixed barrier which holds the dose of powder material in a position distant from the inlet orifice for compressed gas, the tank of said substance is removable, said gas compression means constitute an air pump provided with an inlet check valve and with resilient return means, said length of narrowed section of the intermediate channel includes an end which flares towards the inlet orifice of the tank, the plug is urged by resilient return means for the plug towards a position in which it closes said flared end of the length of narrowed section, and said flared end has a cone angle that is small enough to enable the plug to be jammed in said flared end solely under drive from the resilient plug return means. Advantageously, the half-angle at the apex of the said flared end is less than or equal to 10°. Said fixed barrier may constitute said means for limiting the movement of the plug, and said means for guaranteeing that compressed gas can flow may include at least one opening passing through said fixed barrier.

Other characteristics and advantages of the invention appear on reading the following description of various embodiments of the invention, given by way of non-limiting example and made with reference to the accompanying drawings.

In the drawings:

FIG. 4 is a view analogous to FIG. 1 for another embodiment of the device of the invention;

FIG. 5 is a detail view of FIG. 4 on a larger scale;

FIG. 6 is a section view on line VI—VI of FIG. 5; and

Figure 1:
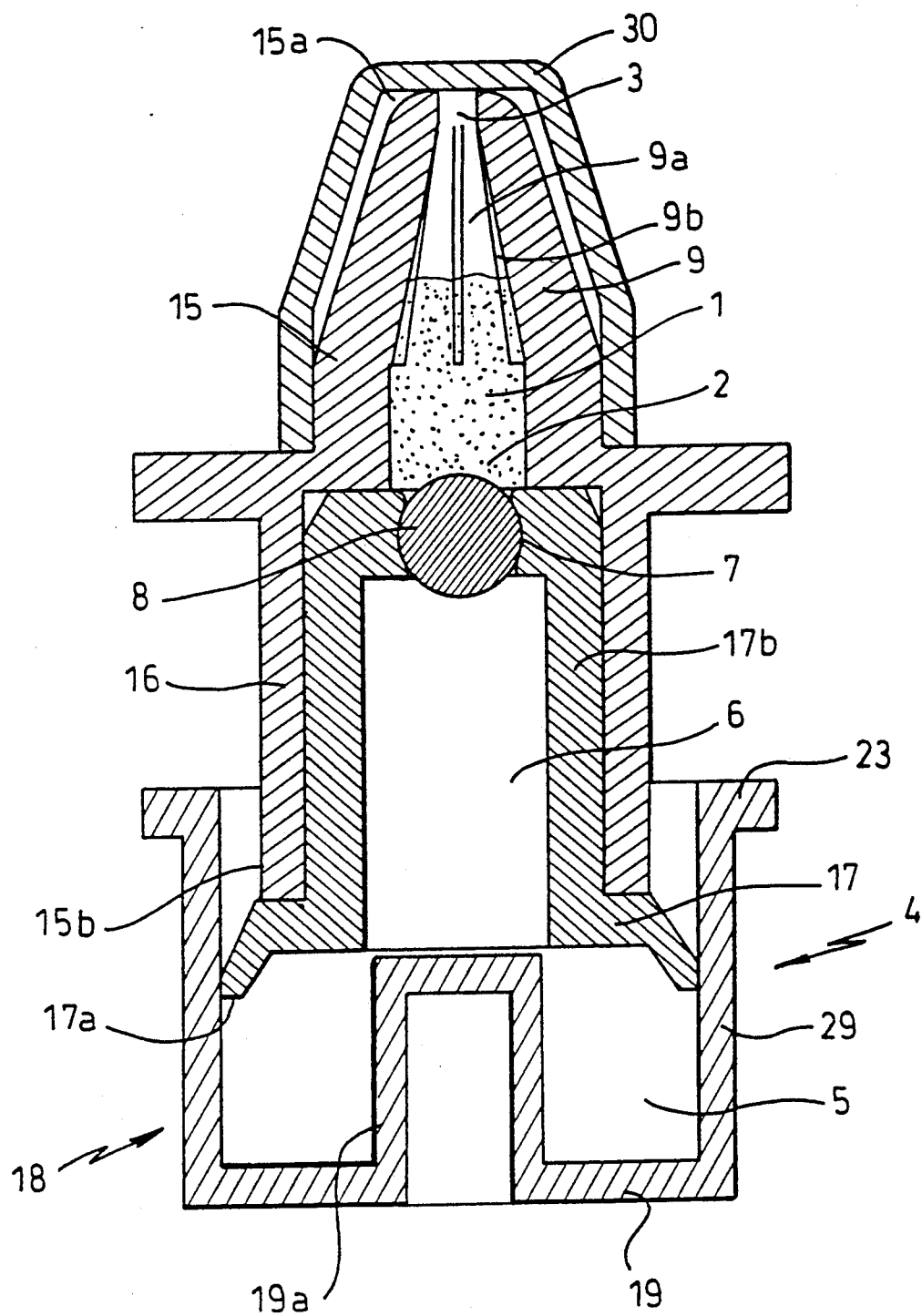
FIG. 1 is a section view through a first embodiment of the device of the invention.

With reference to FIG. 1, in a first embodiment of the invention, the device comprises a pusher endpiece 15 which delimits a tank 1 containing a substance to be sprayed, e.g. a solid powder material. This solid powder material is generally a medicine for nasal use. The endpiece 15 extends axially from a front end 15a to a rear end 15b. At its front end 15a, the endpiece 15 includes an outlet orifice 3 which communicates with the tank 1 of substance. The endpiece 15 has a radially outwardly extending flange 22 which serves as a bearing point for the fingers of a user. The pusher-endpiece 15 includes a frustoconical wall 9 that converges towards the outlet orifice 3 and that extends between the front end 15a and the outer radial flange 22. In addition, the pusher-endpiece 15 includes a cylindrical wall 16 which extends axially from the flange 22 to the rear end 15b. In addition, the frustoconical wall 9 includes an inside surface having axial ribs 9b formed therein for a purpose explained below. The pusher-endpiece 15 as described may be molded out of thermoplastic material.

When the device of the invention is stored prior to use, the leading end 15a of the pusher-endpiece 15 is covered by a cap 30 which may be made of plastics or of any other material, and which is fixed to the pusher-endpiece 15 by being a push-fit, by snap-fastening, by screwing, or by any other means.

The device of the invention also includes a piston 17 which is received inside the cylindrical wall 16 of the pusher-endpiece. The piston 17 has a peripheral sealing lip 17a that projects radially outwards from the cylindrical wall 16 in the vicinity of the rear end 15b of the pusher-endpiece, and a fixing rod 17b has an axial central channel 6 passing therethrough and communicating with the tank 1 of substance. The axial channel has a length 7 of narrowed section which defines an inlet orifice 2 to the tank 1. A bead or plug of some other shape is received as a force-fit in the length 7 so as to close the inlet orifice 2 of the tank 1 of substance. The piston 17 is advantageously molded in a relatively flexible thermoplastic material, e.g. polyethylene. The bead may be made, for example, of stainless steel or else of high density polyethylene.

The device of the invention also includes a cylinder 18 which may be molded out of plastics material. The cylinder 18 has an end wall 19 and a cylindrical side wall 29 which extends axially between the end wall 19 and an open end 23. The peripheral sealing lip 17a of the piston 17 slides in sealed manner inside the cylindrical side wall 22. The piston 17 and the cylinder 18 thus define a compression system 14 which contains a supply of gas 5 that may be constituted by air or by some other gas. Advantageously, the end wall 19 of the cylinder 18 may include a central portion 19a that projects towards the central channel 6 of the piston and that is adapted to penetrate into said central channel 6 when the device is actuated, thereby increasing the pressure that exists in the supply of gas 5 during actuation.

When it is desired to use the device of the invention, its cap 30 is removed and the front end 15a of the pusher-endpiece is inserted into a nostril, after which pressure is applied against the end wall 19 of the cylinder 18 while holding the flange 18 by means of two fingers, thereby increasing the pressure of the gas in the supply 5. When the gas pressure reaches a predetermined value that depends on how firmly the bead 8 is clamped in the narrowed length 7, the bead is ejected into the tank 1 so that the gas compressed in the supply 5 can escape and entrain the powder contained in the tank 1. The bead 8 is in no danger of blocking the outlet orifice 3 because of the ribs 19a situated inside the frustoconical wall 9.

This embodiment is particularly advantageous insofar as the piston 17 can be made of a flexible material, thereby ensuring good sealing both between the piston 17 and the cylinder 18 and between the piston 17 and the bead 8, thus also ensuring that the bead 8 is properly clamped resiliently within the narrowed length 7.

Advantageously, the shape of the frustoconical wall 9 and the diameter of the outlet orifice 3 are such that once the cap has been removed and while the device is being handled prior to being actuated, the dose of powder contained in the tank 1 is retained therein by a bridging effect inside the tank 1, i.e. by means of a phenomenon similar to that which sometimes occurs accidently in storage silos for powder materials. In this way, even if the orifice 3 happens to be pointing downwards after the cap has been removed, the dose of powder inside the tank 1 does not escape through the orifice 3 prior to the device being actuated. The diameter of the orifice 3 may be less than or equal to 1.5 mm, and may advantageously be about 1 mm, possibly even being less than 1 mm or 0.5 mm, when using conventional pharmaceutical powders for spraying into the nose.

Figure 2:
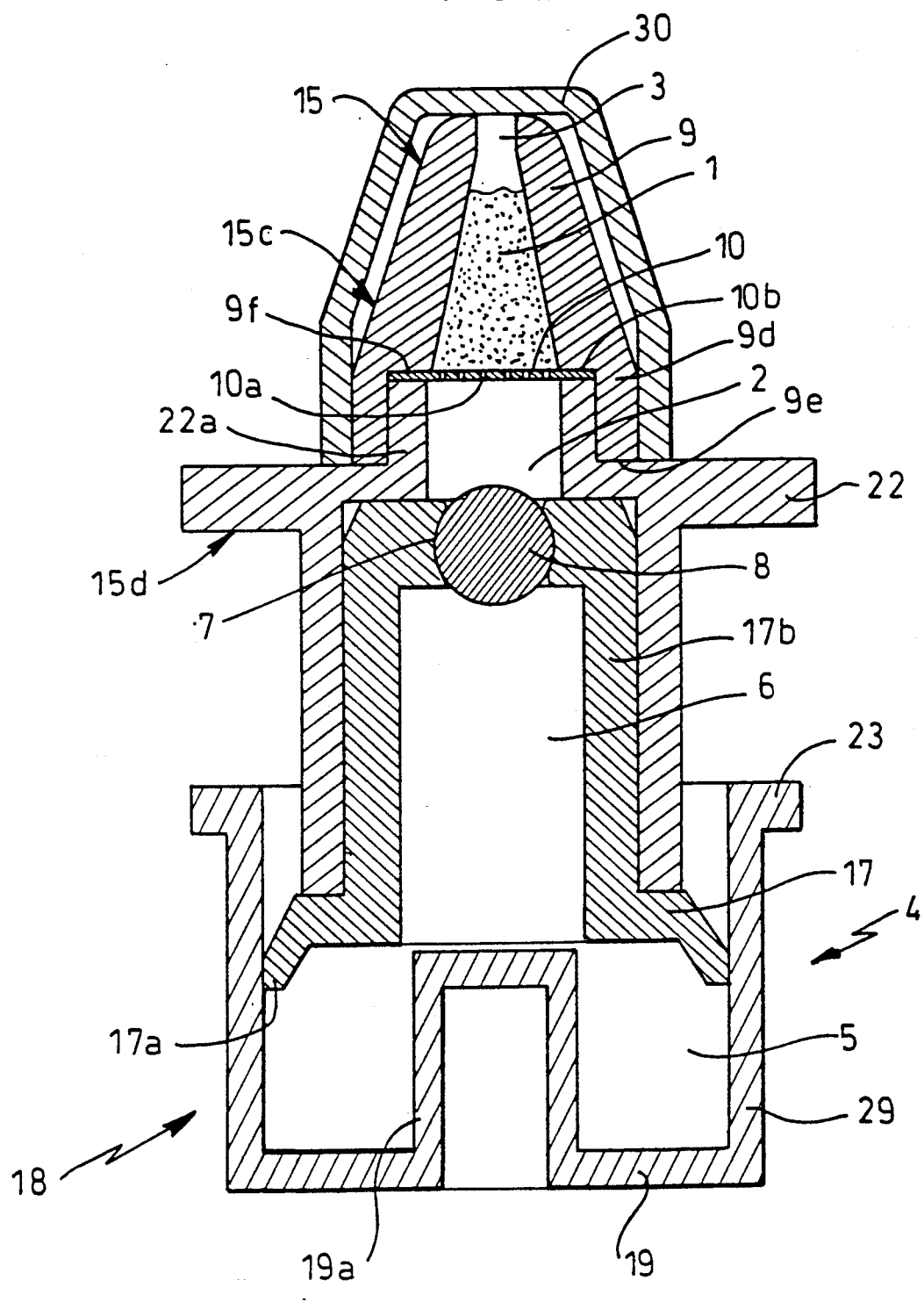
FIG. 2 is a view analogous to FIG. 1 for another embodiment of the device of the invention.

FIG. 2 shows a variant of the FIG. 1 device. The general structure of the FIG. 2 device is similar to the structure of the FIG. 1 device, such that the FIG. 2 device is not described again in detail. The FIG. 2 device differs from the FIG. 1 device in that the frustoconical wall 9 of the pusher-endpiece 15 no longer includes an inside rib 9b. In addition, the pusher-endpiece 15 is formed, in this case, in two portions, a front portion 15c including the frustoconical wall 9 and a rear portion 15d including the flange 22 and the cylindrical wall 16. The frustoconical wall 9 extends axially towards the flange 22 by means of a short cylindrical wall 9d that extends to an axial end 9e, thereby forming an inside shoulder 9f. In addition, the flange 22 includes a cylindrical wall 22a which is adapted to engage inside the cylindrical wall 9d. The cylindrical wall 9d may be fixed to the inside of the cylindrical wall 22a by being a force-fit, by snap-fastening, by screwing, or by any other means.

The device also includes a fine-mesh grid 10 having a periphery 10b that is pinched between the shoulder 9f and the cylindrical wall 22a. The grid 10 may be constituted by metal wires that cross over one another and that are fixed together or else it may be implemented in the form of a metal plate or a plastics plate that is pierced with holes 10a. The size of the holes 10a is small enough to prevent the powder contained in the tank 1 passing through them. The dose of powder is thus delimited by the frustoconical wall 9 and the grid 10, and it is kept away from the bead 8.

When the device is actuated, the bead 8 strikes against the grid 10 suddenly. The kinetic energy stored by the bead 8 is sufficient to create a shock that lifts the dose of powder off the grid 10, thereby facilitating the passage of gas through the grid 10. In addition, the shock has the effect of breaking up the powder contained in the tank 1, thereby facilitating subsequent entrainment thereof by the flow of compressed gas. In addition, the shock breaks the "bridging" of the dose of powder about the outlet orifice 3, i.e. it eliminates the bridging effect that could otherwise prevent the powder from leaving via the orifice 3.

Since the dose of powder is kept away from the bead 8 by the grid 10, it is also possible to ensure that the flow of compressed gas through the entire section of the tank 1 is uniformly distributed so that the entire dose is entrained by the flow of compressed gas: this prevents dead volumes being created that are not swept out by the flow of compressed gas.

Advantageously, the grid 10 has a degree of flexibility so that the shock of the bead against the grid causes it to be deformed in a manner that tends to open the holes or pores through the grid adjacent to the powder, thereby facilitating the flow of air.

Figure 3:
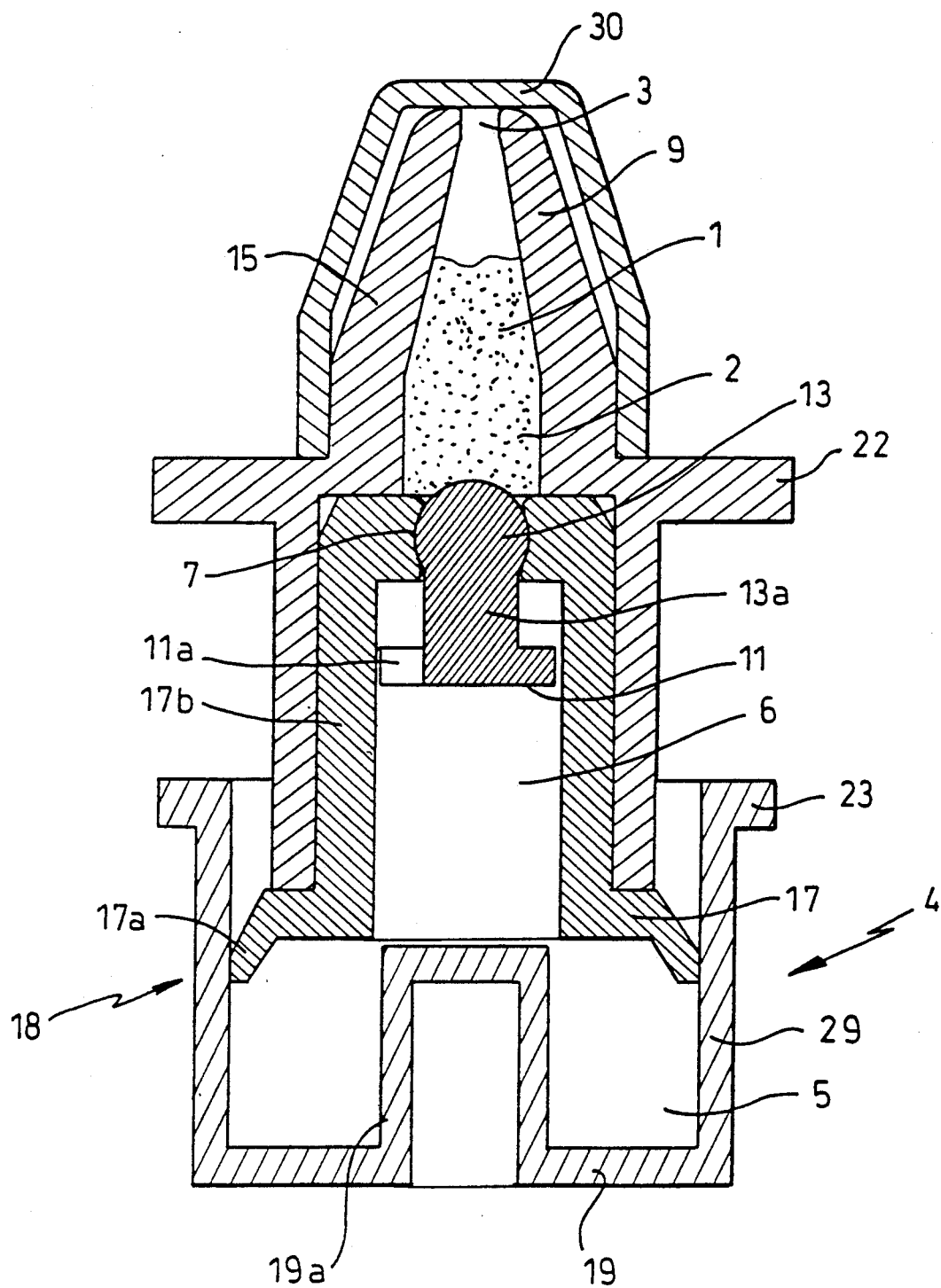
FIG. 3 is a view analogous to FIG. 1 for another embodiment of the device of the invention.

FIG. 3 shows another variant of the FIG. 1 device which is similar in structure and is therefore not described in detail again.

Unlike the FIG. 1 device, this device does not have a bead, but has a plug 13 which projects into the gas supply 5 in the form of a rod 13a fitted with a catch 11 that projects radially outwards. The catch 11 includes passages 11a to allow the flow of compressed gas to pass therethrough. On actuation, the plug 13 is ejected towards the tank of substance 1, but its movement is limited by the catch 11 that comes into abutment against the length 7 of narrowed section in the intermediate channel 6.

FIGS. 4 to 6 show another embodiment of the device of the invention. As shown in FIG. 4, the device includes a syringe 104 provided with a cylindrical supply of gas 105 slidably receiving a piston 117 which is provided with an actuator rod 123. The tank 105 and the actuator rod 123 may both be molded out of plastics material. The piston is advantageously made of elastomer. The syringe 104 has a capillary outlet channel 121 formed in an endpiece 122.

The device also includes a length of tube 124 which extends axially between a first end 124a and a second end 124b. The first end 124a of the length of tube 124 is a force-fit on the endpiece 122 of the syringe 104. The length of tube 124 defines an intermediate channel 106 having a length 107 of narrowed section. A bead is jammed in the length 107 of narrowed section, thereby closing said length 107.

The device also includes an endpiece 115 having a cylindrical side wall 116 which is force-fit in the second end 124b of the length of tube 124, said cylindrical wall 116 extending forwards in the form of a frustoconical wall 109 to an outlet orifice 103. A rod 112 having two axial lateral grooves 112a is a force-fit inside the cylindrical side wall 116.

In addition, in this particular example, a sleeve 127 having a cylindrical outside shape is engaged on the side wall 114 and the frustoconical wall 109 so as to prevent a user being harmed by the pointed end of the frustoconical wall 109.

The sleeve 127 is covered by a cap (not shown) while being stored.

The frustoconical wall 109 and the rod 126 co-operate to define a supply of powder 101 which has an inlet orifice 102. The size of the groove 126a is small enough to ensure that the powder contained in the tank 101 does not enter said groove 126a, and the size of the outlet orifice 103 is small enough to ensure that the powder does not leave via the orifice while the device is being handled prior to actuation, a bridging effect being established as described above. In addition, the length of tube 124, the bead 8, and the capillary channel 121 co-operate to define a supply of liquid 120 which is expelled together with the powder during actuation. The diameter of the capillary channel 121 is small enough to prevent the liquid in the supply 120 penetrating into the supply of gas 105.

Figure 7:
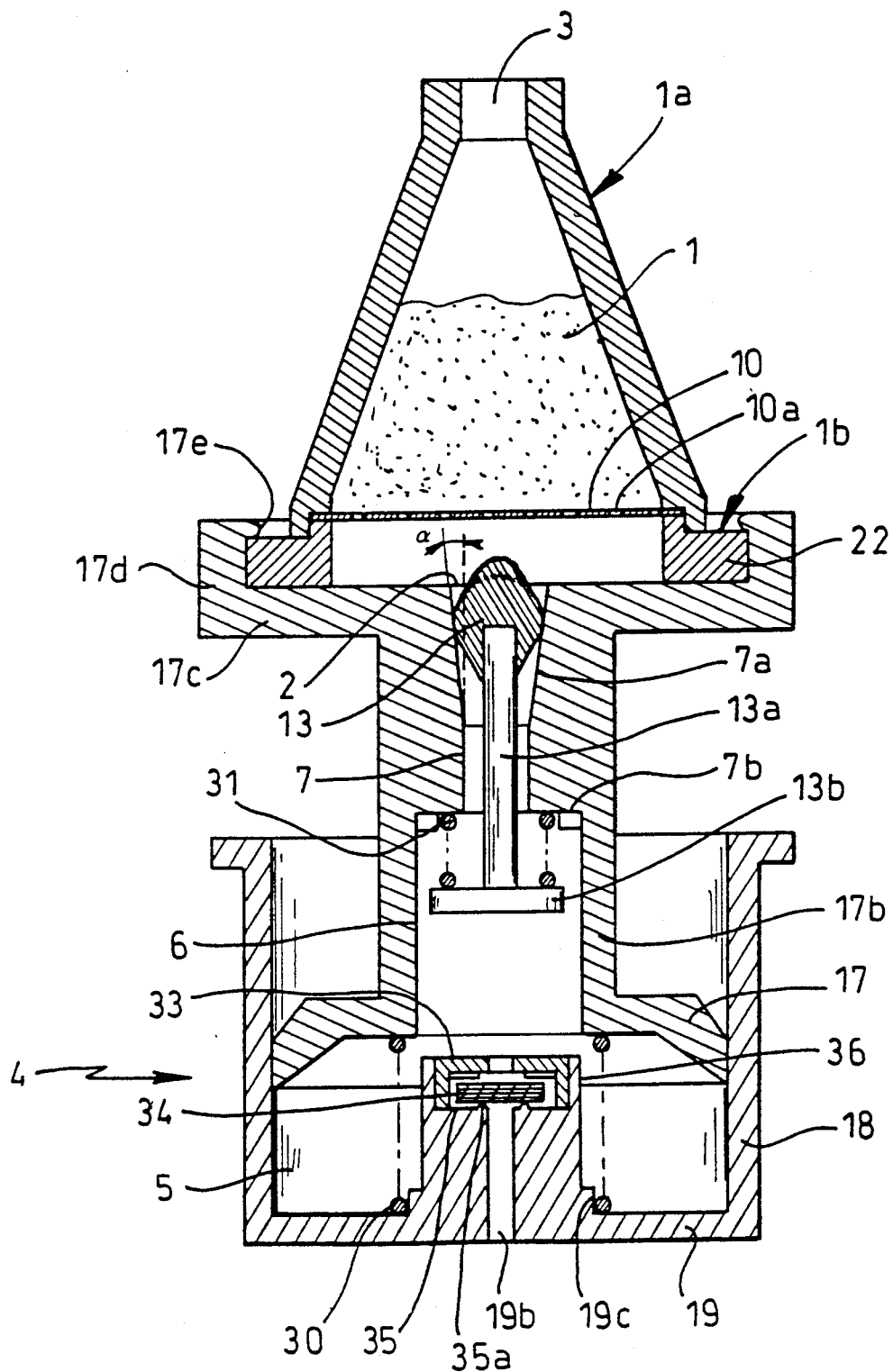
FIG. 7 is a section view through another embodiment of the device of the invention.

The device shown in FIG. 7 is a variant of the device shown in FIG. 2 and it is designed to be rechargeable. The FIG. 7 device includes a removable tank 1 which is made up of two parts. The tank 1 includes a front part 1a and a rear part 1b which are assembled together as a force-fit, by gluing, by snap-fastening, or by any other means, and between them they hold captive a grid 10 similar to the grid described with reference to FIG. 2. The front portion 1a of the tank 1 is generally frustoconical in shape, and has an outlet orifice 3. The tank 1 is designed to contain a substance in powder form, the grid is designed to retain said powder substance inside the front portion 1a, and the shape of the front portion 1a together with the section of the outlet orifice 3 are designed to prevent the powder escaping accidentally while the device is being handled.

The rear portion 1b of the tank 1 includes an outwardly direction radial flange 22.

The device further includes an air pump 4 comprising a cylinder 18 and a piston 17 sliding in the cylinder. The piston and the cylinder together define a pump chamber 5, and a return spring 30 is interposed between them. The cylinder 18 includes an end wall 19 provided with an air inlet opening 19b which is in communication with an inlet check valve. In the example shown, the inlet orifice 19b opens out into the cylinder 18, in the center of a substantially radial surface 35. A sealing rim 35a is formed on the surface 35 around the outlet from the inlet orifice 19b. The radial surface 35 is surrounded by an axial cylindrical wall 36 which receives a valve member carrier 33. A flat gasket 34 of elastomer is held captive between the carrier 33 and the radial surface 35, said gasket 34 being adapted to bear in sealed manner against the sealing rim 35a when higher pressure exists inside the cylinder 18. Examples of such inlet valves are disclosed in Document EP-AP-0 377 536 and in corresponding American patent U.S. Pat. No. 4,966,535. The end wall 19 has projections 19c for centering the spring 30.

The piston 17 has a hollow rod 17b which defines an intermediate channel between the air pump 4 and the tank 1. The rod 17b extends axially towards the tank 1 up to a flange 17c which projects radially outwards. The flange 17c is extended axially towards the tank 1 by a cylindrical side wall 17b which extends to snap-fastening means 17e. The snap-fastening means 17e may be constituted by an inside rib, for example. The flange 22 of the tank 1 is received inside the cylindrical side wall 17d and it is held in contact with the flange 17c by the snap-fastening means 17e. The flange 22 of the tank 12 is in sealed contact with the cylindrical side wall 17d of the ring 17c. Advantageously, the piston 17 is made of a relatively flexible material such as polyethylene, so that the sealing between the flange 22 and the cylindrical side wall 17 can be obtained by the flange 22 being resiliently clamped inside the cylindrical wall 17d.

As in the preceding examples, the intermediate channel 6 has a length 7 of narrowed section in the vicinity of the tank 1. The length 7 defines an inlet orifice 2 for the tank 1. In the example shown, the length 7 of narrowed section has an enlarged end 7b in the vicinity of the tank 1 flaring towards the tank 1. The end 7b is thus conical in shape, having a conical half-angle α that is preferably less than or equal to 10°. In addition, the length 7 of narrowed section also defines a shoulder 7a that is directed towards the end wall 19 of the cylinder 18.

The device also includes a plug 13 which is jammed in the flared end 7b of the length 7. A rod 13a is a force-fit in said plug 13, and said rod extends axially towards the end wall 19 of the cylinder 18, as far as a flange 13b disposed inside the largest portion of the intermediate channel 6. A plug return spring 31 is disposed between the shoulder 17a and the flange 13b. The return spring 31 is generally of low stiffness so as to avoid impeding displacement of the plug 13 towards the tank 1 during actuation. In addition, the rod 13a is sufficiently long to enable the plug 13 to strike the grid 10 during actuation. Finally, because of the small cone angle of the flared end 7b of the intermediate channel, the plug 13 jams itself in the flared end 7b after each actuation merely under drive from the plug return spring 31, in spite of the small stiffness of the said spring 31.

We claim:

1. A compressed gas device for spraying a single dose of a fluid substance in finely divided form, the device comprising:

a tank (1, 101) containing said single dose, said tank having an inlet orifice (2, 102) for compressed gas and an outlet orifice (3, 103);

manually-actuated gas compression means (4, 104), said gas compression means (4, 104) comprising a supply of gas (5, 105) communicating with the inlet orifice (2, 102) of the tank (1, 101) via an intermediate channel (6, 16) said intermediate channel including a length of narrowed section (7, 107), said length of narrowed section being closed in sealed manner by a plug (8, 103) which is held in said length of narrowed section so that when the pressure of the gas contained in the supply of gas (5, 105) reaches a predetermined threshold, said plug (8, 103) is expelled from said length of narrowed section (7, 107) towards the tank (1, 101) of substance, thereby opening said intermediate channel (6, 106);

the device including means (9, 10, 11, 112) for limiting the displacement of the plug (8, 13) towards the outlet orifice of the tank of said substance, thereby defining an abutment position for the plug;

the device being characterized in that said means (9, 10, 11, 112) for limiting displacement of the plug include means (9c, 10a, 11a, 112a) for guaranteeing that the compressed gas can continue to flow when the plug is in its abutment position.

2. A device according to claim 1, wherein the tank of said substance (1) includes a convergent portion (9) which converges towards the outlet orifice (3), said convergent portion (9) constituting said means for limiting the displacement of the plug, and said convergent portion (9) including ribs (9b) constituting said means (9c) for guaranteeing that the compressed gas can flow.

3. A device according to claim 1, wherein the substance is a solid powder material, the tank of said substance (1) includes a fixed barrier (10, 112) which holds the dose of powder material in a position that is distant from the inlet orifice (2) for compressed gas, said fixed barrier constituting said means for limiting the displacement of the plug, and said means for guaranteeing that the compressed gas can flow include at least one opening (10a, 112a) through said fixed barrier.

4. A device according to claim 3, wherein when the plug (8) comes into contact with said fixed barrier (10, 112), and said plug has sufficient kinetic energy to shock the fixed barrier to cause the dose of powder material to be unstuck from said fixed barrier.

5. A device according to claim 3 or 4, wherein said fixed barrier is an element in the form of a diaphragm (10).

6. A device according to claim 5, wherein the diaphragm (10) has a degree of flexibility.

7. A device according to claim 3 or 4, wherein said fixed barrier includes a solid central rod (112) provided with at least one axial lateral groove (112a) constituting the at least one opening for allowing the compressed gas to flow.

8. A device according to claim 1, wherein the plug (13) includes an enlarged catch (11) which co-operates with the length of narrowed section (7) of the intermediate channel (6) to limit the movement of the plug towards the tank (1) of substance, said catch including at least one opening (11a) which constitutes said means for guaranteeing that the compressed gas can flow.

9. A device according to claim 1, wherein said substance is a solid powder material, and when said means (9, 10, 11, 112) for limiting the displacement of the plug stop displacement of said plug, said plug possesses sufficient kinetic energy to transmit a shock to said powder material that ensures that said powder material breaks up.

10. A device according to claim 1, wherein said substance is a solid powder material, said tank of said substance (1, 101) includes a convergent portion (9, 109) that converges towards the outlet orifice (3, 103), said convergent portion being of a shape and the outlet orifice being of a section that are adapted to enable the powder material to be retained by a bridging effect in the vicinity of the outlet orifice while the device is being handled prior to being actuated.

11. A device according to claim 10, wherein when said means (9, 10, 11, 112) for limiting the displacement of the plug stop the displacement of the plug, said plug possesses sufficient kinetic energy to transmit a shock to said powder material that breaks the bridging of the powder material and thus facilities spraying of the powder material through the outlet orifice (3, 103) by the flow of compressed gas.

12. A device according to claim 10, wherein the outlet orifice (3, 103) has a diameter that is less than or equal to 1.5 mm.

13. A device according to claim 10, wherein the outlet orifice (3, 103) has a diameter that is less than or equal to 1 mm.

14. A device according to claim 10, wherein the outlet orifice (3, 103) has a diameter that is less than or equal to 0.5 mm.

15. A device according to claim 1, wherein:
the tank (3) of said substance is included in a pusher-endpiece (15) having a hollow cylindrical rear portion (16) in communication with the compressed gas inlet orifice (2) of the tank (3);
the gas compression means (4) include a hollow piston (17) which is engaged in the rear portion (16) of the pusher-endpiece (15), and a cylinder (18) provided with an end wall (19), the cylinder (18) sliding axially over the piston (16); and
the hollow piston (17) defines the intermediate channel (6).

16. A device according to claim 15, wherein the hollow piston (17) is made of a flexible thermoplastic material.

17. A device according to claim 16, wherein the said flexible thermoplastic material is polyethylene.

18. A device according to claim 1, wherein the said intermediate channel (106) includes a supply of liquid (120) and liquid-retaining means (121) are disposed between the plug and the supply of gas (4).

19. A device according to claim 18, wherein the liquid-retaining means are constituted by a capillary channel (121).

20. A device according to claim 1, wherein the substance is a solid powder material, the tank of substance (1) includes a fixed barrier (10) which holds the dose of said powder material in a position distant from the inlet orifice for compressed gas (2), the tank (1) of said substance is removable, said gas compression means (4) constitute an air pump provided with an inlet check valve (33, 34) and resilient return means (30), said length of narrowed section (7) of the intermediate channel (6) includes an end (7b) which flares towards the inlet orifice (2) of the tank, the plug (13) is urged by a second resilient return means (31) for the plug towards a position in which it closes said flared end (7b) of the length of narrowed section (7), and said flared end (7b) has a cone angle that is small enough to enable the plug (13) to be jammed in said flared end solely under drive from the resilient plug return means (31).

21. A device according to claim 20, wherein the half-angle at the apex of the said flared end is less than or equal to 10°.

22. A device according to claim 20 or claim 21, wherein said fixed barrier (10) constitutes said means for limiting the movement of the plug, and said means for guaranteeing that compressed gas can flow include at least one opening (10a) passing through said fixed barrier.

* * * * *